US00PP28166P3

(12) United States Plant Patent
Olesen

(10) Patent No.: US PP28,166 P3
(45) Date of Patent: Jul. 11, 2017

(54) COMPACT FLORIBUNDA ROSE PLANT NAMED 'POULPAL065'

(50) Latin Name: ***Rosa* hybrid**
Varietal Denomination: Poulpal065

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 12 days.

(21) Appl. No.: 14/756,255

(22) Filed: Aug. 20, 2015

(65) Prior Publication Data

US 2017/0055395 P1 Feb. 23, 2017

(51) Int. Cl.
*A01H 5/02* (2006.01)

(52) U.S. Cl.
USPC ..... Plt./143

(58) Field of Classification Search
USPC ..... Plt./141, 143
See application file for complete search history.

(56) References Cited

PUBLICATIONS

Poulsen Roser A/S "Palace-Perfection by Poulsen" Oct. 2012 (1 page).*

* cited by examiner

*Primary Examiner* — Susan McCormick Ewoldt

(57) ABSTRACT

A new garden rose plant of the Compact Floribunda class which has abundant, yellow pink bicolor flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal065'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpal065', originated as a single seedling from the stated cross.

The new variety may be distinguished from its male pollen parent and female seed parent primarily by the following characteristics. The female seed parent has flowers with a 50 mm diameter, while the new variety has flowers with a 90 mm diameter. The male pollen parent has yellow flowers while the new variety has yellow and pink bicolor flowers.

The objective of the hybridization of this rose variety was to create a new and distinct variety for garden use with unique qualities, such as:

1. Uniform and abundant yellow pink bicolor flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal065' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpal065' was selected in the spring of 2008 by the inventor as a single plant from the progeny of the aforementioned hybridization.

Asexual reproduction of 'Poulpal065' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpal065' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal065'.

Specifically illustrated in FIG. 1 of the drawings are open flowers, petals detached, sepals detached, flower buds, and reproductive flower parts.

Figure 1:
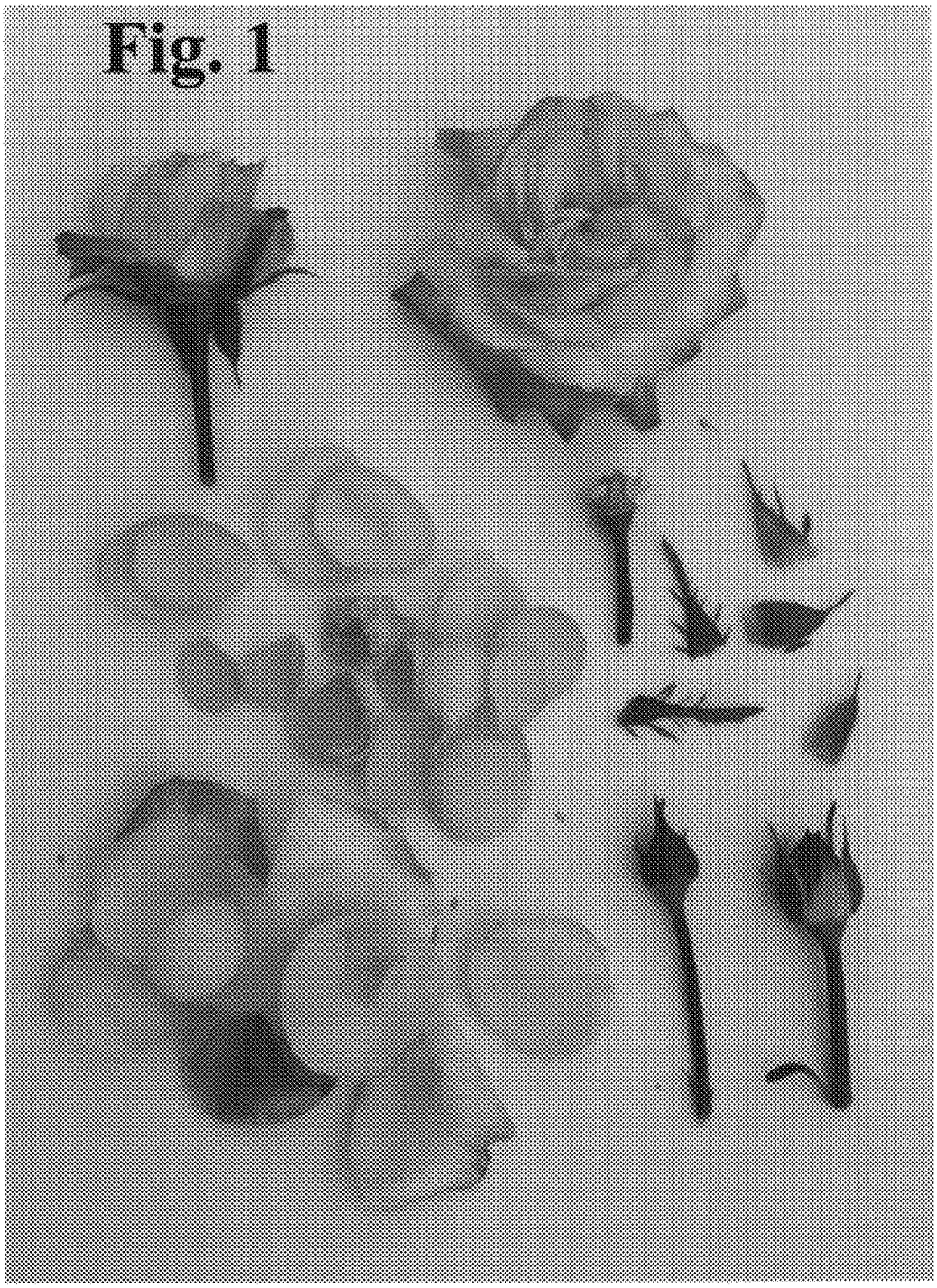
Figure 2:
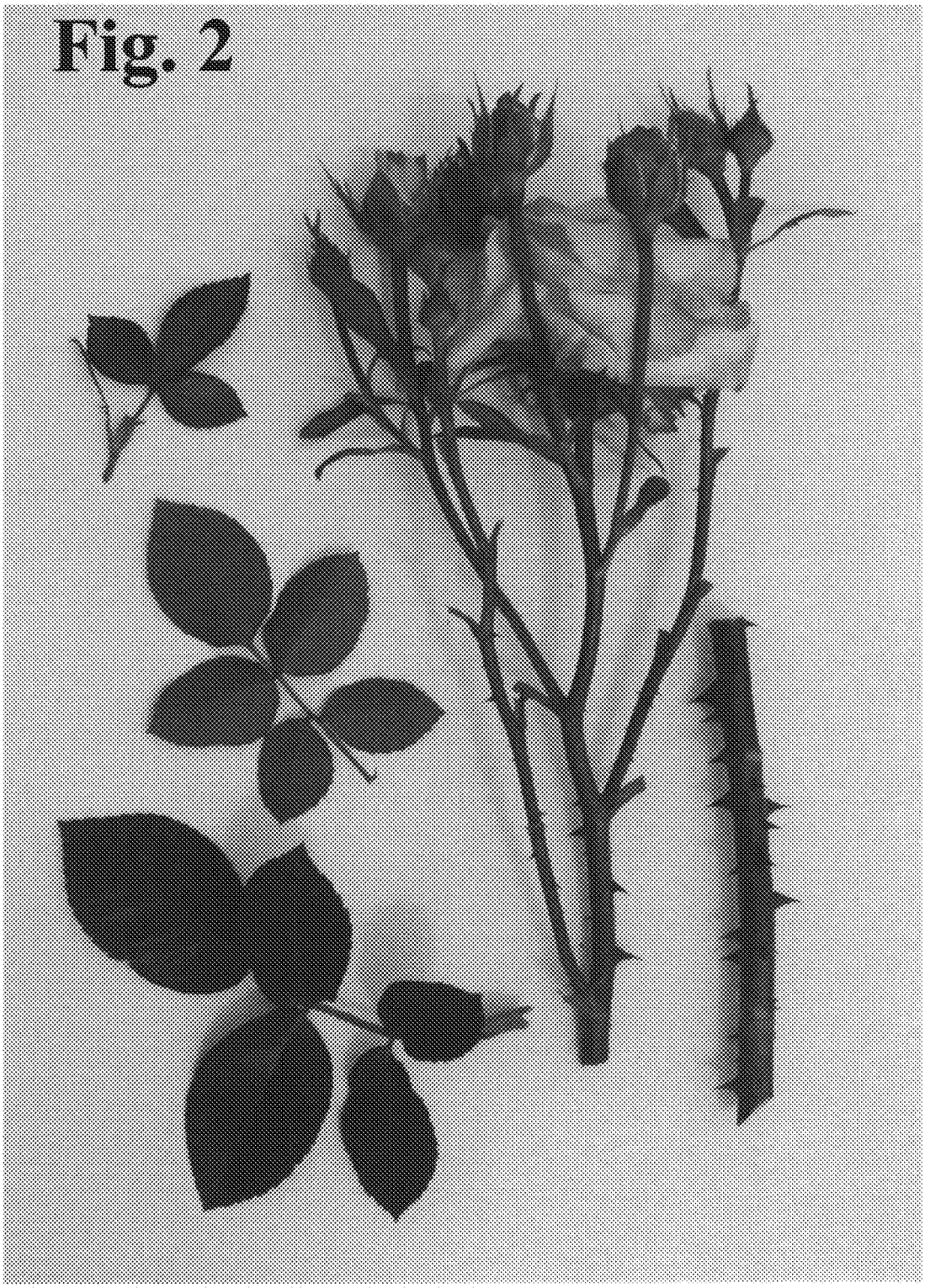

Specifically illustrated in FIG. 2 of the drawings are mature and juvenile leaves, bare stems, and a cluster of flowers at various stages of development. Plants shown are 2 years of age.

DETAILED DESCRIPTION OF THE VARIETY

The following is a description of 'Poulpal065', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpal037', U.S. Plant Pat. No. 24,488 are compared to 'Poulpal065' in Chart 1.

CHART 1

| | 'Poulpal065' | 'Poulpal037' |
|---|---|---|
| Petal Count | 55 | 30 |
| Flower Diameter | 90 mm | 55 mm |
| General Tonality of Flower Color | Yellow Group 6B with intonations of Red Group 36D and Red Group 52C | Yellow-Orange Group 15C with intonations of Red-Purple Group N66A |

FLOWER AND FLOWER BUD

Blooming habit: Continuous.

Flower bud:

*Size.*—Upon opening, 25 mm in length from base of receptacle to end of bud. Bud diameter is 15 mm.

*Bud form.*—Urceolate.

*Bud color.*—As sepals divide petals are Yellow Group 1B and Orange-Red Group N34A.

*Sepal inner surface.*—Color: Yellow-Green Group 146C. Surface: Lightly pubescent.

*Sepal outer surface.*—Color: Yellow-Green Group 144A with intonations of Orange-Red Group 173A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—30 mm long, 15 mm wide.

*Receptacle.*—Texture: Smooth. Size: 8 mm in height, 10 mm wide. Color: Yellow-Green Group 144A. Shape: Funnel.

*Pedicel.*—Surface: Rough. Length: 35 to 45 mm. Diameter: 4 mm on average. Color: Greyed-Purple Group 183B. Strength: Strong.

*Peduncle.*—Length: 5 to 14 cm. Diameter: About 4 mm. Color: Yellow-Green Group 146C with strong intonations of Greyed-Purple Group 187B. Texture: Smooth.

Flower bud development: Flower buds are borne in panicles of about 25 flower buds per stem. Panicles are about 19 cm in diameter.

Flower bloom:

*Fragrance.*—Moderate floral.

*Duration.*—The blooms have a duration on the plant of approximately 15 days. Petals fall cleanly away from plant after flowers have fully matured.

*Size.*—Flower diameter is 90 mm when open. Flower depth is 45 mm.

*Flower shape.*—High centered, double, with a high pointed center which is tightly closed.

*Shape of flower, side view.*—The upper portion is flat. The lower portion is concave.

Petalage: Under normal conditions, flowers have 55 petals total, about 10 of which are petaloids.

General tonality of flower: Open flowers are Yellow Group 6B with intonations of Red Group 36D and Red Group 52C. Flowers change tonality with age, to Yellow Group 8D with intonations of Red Group 36D and Red Group 52C.

Petal color:

*Upon opening, outer petals.*—Upper surface: Marginal zone Red Group 51A. Middle zone Red Group 36D. Basal zone Yellow Group 6B. Lower surface: Marginal zone Red Group 51A. Middle zone Red Group 36D. Basal zone Yellow Group 6B.

*Upon opening, inner petals.*—Upper surface: Yellow Group 12B with marginal intonations of Yellow-Orange Group 16A. Lower surface: Yellow Group 12B at the basal and middle zone. Yellow Group 12C at the marginal zone.

*After opening, outer petals.*—Upper surface: Marginal zone Red Group 48B. Middle zone Red Group 49D. Basal Zone Yellow Group 5C. Lower surface: Marginal zone Red Group 36A. Middle zone Orange Group 27D. Basal Zone Yellow Group 5D.

*After opening, inner petals.*—Upper surface: Yellow Group 10A. Lower surface: Yellow Group 10A.

Petals:

*Petal reflex.*—Moderately reflexed.

*Margin.*—Entire and uniform. Moderate undulations.

*Shape.*—Generally broad elliptical. Apex shape: Rounded. Base shape: Acute.

*Size.*—40 mm (l)×50 mm (w).

*Texture.*—Smooth.

*Thickness.*—Below average.

Petaloids:

*Size.*—30 mm (l) by 15 mm (w).

*Quantity.*—About 10.

*Shape.*—Elliptical, with an acute base and rounded apex.

*Color.*—Yellow Group 12B with marginal intonations of Yellow-Orange Group 16A at the upper surface. The lower surface is Yellow Group 12B at the basal and middle zone. Yellow Group 12C at the marginal zone.

Reproductive flower parts:

*Pollen.*—None observed.

*Anthers.*—Size: 2 mm in length. Color: Yellow Group 5A. Quantity: 55 on average.

*Filaments.*—Color: Yellow-Green Group 154A. Length: 4 mm.

*Pistils.*—Length: 6 mm. Quantity: 30 on average.

*Stigmas.*—Color: Greyed-Yellow Group 160B.

*Styles.*—Color: Green-White Group 157A.

*Location of stigmas.*—Superior in location relative to the length of the filaments and the height of the anthers.

*Hips.*—None observed to date.

PLANT

Plant growth: Upright, bushy. Plants are 60 cm in height, and 30 cm wide.

Stems:

*Color.*—Juvenile growth: Yellow-Green Group 146C with strong intonations of Greyed-Purple Group 187B. Mature growth: Yellow-Green Group 146B with strong intonations of Greyed-Purple Group 183B.

*Length.*—On average, canes are 25 cm from the base of the plant to the flowering portion.

*Diameter.*—9 mm.

*Internodes*.—On mature canes about 30 mm between nodes.

*Surface texture*.—Young wood: Rough. Older wood: Rough.

Long prickles:

*Incidence.*—15 to 20 prickles per 10 cm of stem.

*Size*.—Average length of prickles on mature stems is 10 mm.

*Shape*.—Upper portion is linear. Lower portion is concave.

*Color*.—Juvenile prickles: Greyed-Purple Group 183A. Mature prickles: Greyed-Purple Group 183A.

Plant foliage:

*Compound leaf:* 140 mm (l)×40 (w).

*Quantity.*—2 or 3 leaves per 10 cm of stem on average.

*Color of juvenile foliage*.—Upper side: Yellow-Green Group 147A. Lower side: Yellow-Green Group 147B. Anthocyanin: Greyed-Purple Group 183A.

*Color of mature foliage*.—Upper side: Yellow-Green Group 147A. Lower side: Yellow-Green Group 146B.

Plant leaves and leaflets:

*Stipules*.—Size: 30 mm long, 10 mm wide. Quantity: 2 per compound leaf. Shape: Linear, slightly broad based with outward extending apices. Margins: Finely serrated. Color: Green Group 143A.

*Petiole*.—Length: 40 mm. Diameter: 2 mm.

*Upper surface*.—Color: Yellow-Green Group 144B.

*Lower surface*.—Color: Yellow-Green Group 144C with Greyed-Purple Group 183C.

*Rachis*.—Length: 30 mm. Upper surface: Color: Yellow-Green Group 144B.

*Lower surface*.—Color: Yellow-Green Group 144C with Greyed-Purple Group 183C. Texture: Small prickles.

*Leaflet*.—Quantity: Normally 5 leaflets. Margins: Serrated. Size: On average terminal leaflets are 60 mm long, 40 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium sps*., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal065', substantially as illustrated and described herein, due to its abundant yellow pink bicolor flowers, disease resistance, and extended period of bloom.

* * * * *